(12) United States Patent
Lange et al.

(10) Patent No.: US 11,213,474 B2
(45) Date of Patent: Jan. 4, 2022

(54) COSMETIC AGENT FOR TEMPORARY DEFORMATION OF KERATINIC FIBERS USING POLYMER COMBINATION II

(71) Applicant: Henkel AG & Co. KGaA, Duesseldorf (DE)

(72) Inventors: Julia Bibiane Lange, Bad Bramstedt (DE); Diane Metten, Hamburg (DE); Cyrielle Martinez, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 180 days.

(21) Appl. No.: 16/597,398

(22) Filed: Oct. 9, 2019

(65) Prior Publication Data

US 2020/0113804 A1    Apr. 16, 2020

(30) Foreign Application Priority Data

Oct. 11, 2018   (DE) .................... 10 2018 217 401.6

(51) Int. Cl.
*A61Q 5/06*   (2006.01)
*A61K 8/81*   (2006.01)
*A61K 8/73*   (2006.01)
*B65D 83/14*  (2006.01)

(52) U.S. Cl.
CPC ............ *A61K 8/8147* (2013.01); *A61K 8/731* (2013.01); *A61K 8/736* (2013.01); *A61K 8/737* (2013.01); *A61K 8/8152* (2013.01); *A61Q 5/06* (2013.01); *B65D 83/14* (2013.01); *A61K 2800/5426* (2013.01)

(58) Field of Classification Search
None
See application file for complete search history.

(56) References Cited

U.S. PATENT DOCUMENTS

2017/0273889 A1*  9/2017  Knappe ................. A61K 8/736

FOREIGN PATENT DOCUMENTS

| DE | 102007053955 A1 | 5/2009 |
| WO | 2009059813 A2   | 5/2009 |
| WO | 2018153658 A1   | 8/2018 |

\* cited by examiner

*Primary Examiner* — Jyothsna A Venkat
(74) *Attorney, Agent, or Firm* — Lorenz & Kopf, LLP

(57) ABSTRACT

The application describes a cosmetic agent for temporary deformation of keratinic fibers. The cosmetic agent includes, in a cosmetically acceptable carrier, a) at least one copolymer A formed from at least one monomer A1 selected from acrylic acid and/or methacrylic acid and at least one monomer A2 selected from acrylic acid esters and/or methacrylic acid esters, b) at least one cationic polymer B different from copolymer A selected from cationic guar derivatives, c) at least one polymer C different from copolymer A and polymer B, selected from cationic cellulose derivatives, and d) at least one propellant.

4 Claims, No Drawings

COSMETIC AGENT FOR TEMPORARY DEFORMATION OF KERATINIC FIBERS USING POLYMER COMBINATION II

CROSS-REFERENCE TO RELATED APPLICATION

This application claims priority to German Patent Application No. 10 2018 217 401.6, filed Oct. 11, 2018, which is incorporated herein by reference in its entirety.

TECHNICAL FIELD

The application relates to cosmetic agents and products for temporary deformation of keratinic fibers using an acrylate copolymer and a cationic guar compound and their use. The application also describes a method using the cosmetic agent.

BACKGROUND

The temporary design of hairstyles for a longer period of time up to several days usually requires the application of firming active ingredients. Corresponding agents for temporary deformation usually contain synthetic polymers and/or waxes as a firming active ingredient. Agents for supporting the temporary transformation of keratinic fibers can be formulated, for example, as a hair spray, hair wax, hair gel, hair foam.

The most important property of an agent for temporary deformation of hair, hereinafter also referred to as a styling agent, is to give the treated fibers the strongest possible hold in the newly modeled shape, that is, a shape impressed on the hair. One also speaks of strong hairstyle hold or the high degree of hold of the styling agent. The hairstyle hold is substantially determined by the type and amount of firming active ingredient used, wherein, however, further constituents of the styling agent can also have an influence.

Styling agents must meet a whole series of other requirements in addition to a high degree of hold. These can be roughly subdivided into properties on the hair, properties of the respective formulation, for example, properties of sprayed aerosols, and properties relating to the handling of the styling agent, wherein the properties on the hair are accorded particular importance. Particularly noteworthy are moisture resistance, low tack and a balanced conditioning effect. Furthermore, a styling agent should be universally applicable for all hair types and mild to hair and skin.

A variety of synthetic polymers which are used in styling agents have already been developed as firming active ingredients to meet the different requirements.

WO 2009/059813 A2 discloses features for temporary deformation of keratinic fibers containing a special combination of polymers. The polymer combination can comprise, for example, an acrylate copolymer and a cationic guar compound.

Although suitable polymers and polymer combinations have been developed for use in the field of temporary hair deformation for quite some time, the results achieved so far still leave further room for improvement, in particular with regard to storage stability, applicability and the degree of hold of these agents. In particular, currently available styling agents can still be improved to the extent that a good combination of degree of hold and long-term hold (high-humidity curl retention) is not always sufficiently guaranteed.

BRIEF SUMMARY

It was an object of the present disclosure to provide further suitable active ingredient combinations which are distinguished by good film-forming and/or firming properties, having a very high degree of hold, without having to forego flexibility and good moisture resistance, in particular perspiration and water resistance.

This object is achieved by a cosmetic agent for temporary deformation of keratinic fibers, containing in a cosmetically acceptable carrier a) at least one copolymer A, formed from
  a1) at least one monomer A1 selected from acrylic acid and/or methacrylic acid, and
  a2) at least one monomer A2 selected from acrylic acid esters and/or methacrylic acid esters,
b) at least one cationic polymer B different from copolymer A selected from cationic guar derivatives,
c) at least one polymer C different from copolymer A and polymer B, selected from cationic cellulose derivatives, and
d) at least one propellant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The (co)polymers A to B per se are known. The combination of the three components a) to c) leads to a strong increase in the moisture resistance and the degree of hold of the agent, without being impaired in their washability.

In principle, keratinic fibers are understood to mean all animal hairs, for example, wool, horsehair, angora hair, furs, feathers and products or textiles made thereof. Preferably, however, the keratinic fibers are human hair, in particular head and/or beard hair.

The agent contains at least one copolymer A as the first constituent essential to the present disclosure. This copolymer has at least one monomer component A1 selected from acrylic acid and/or methacrylic acid, and at least one monomer component A2 selected from acrylic acid esters and/or methacrylic acid esters. The copolymer A can also have further structural units which are polymerized by the addition of corresponding monomers in the polymerization.

Particularly preferred is monomer A1 selected from acrylic acid and/or methacrylic acid and the monomer A2 selected from acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid octyl ester, methacrylic acid octyl ester, acrylic acid decyl ester, methacrylic acid decyl ester, acrylic acid lauryl ester, methacrylic acid lauryl ester, acrylic acid myristyl ester, methacrylic acid myristyl ester, acrylic acid cetyl ester, methacrylic acid cetyl ester, acrylic acid stearyl ester, methacrylic acid stearyl ester, acrylic acid eicosyl ester and methacrylic acid eicosyl ester, most preferably from acrylic acid, methacrylic acid, acrylic acid methyl ester, methacrylic acid methyl ester, acrylic acid ethyl ester, methacrylic acid ethyl ester, acrylic acid lauryl ester, methacrylic acid lauryl ester, acrylic acid stearyl ester and methacrylic acid stearyl ester.

Particularly preferred copolymers A are:
copolymers of acrylic acid with acrylic acid methyl ester,
copolymers of acrylic acid with methacrylic acid methyl ester,
copolymers of acrylic acid with acrylic acid ethyl ester,
copolymers of acrylic acid with methacrylic acid ethyl ester,
copolymers of acrylic acid with acrylic acid propyl ester,
copolymers of acrylic acid with methacrylic acid propyl ester,
copolymers of acrylic acid with acrylic acid isopropyl ester,
copolymers of acrylic acid with methacrylic acid isopropyl ester,
copolymers of acrylic acid with acrylic acid octyl ester,
copolymers of acrylic acid with methacrylic acid octyl ester,
copolymers of acrylic acid with acrylic acid decyl ester,
copolymers of acrylic acid with methacrylic acid cc decyl ester,
copolymers of acrylic acid with acrylic acid lauryl ester,
copolymers of acrylic acid with methacrylic acid lauryl ester,
copolymers of acrylic acid with acrylic acid myristyl ester,
copolymers of acrylic acid with methacrylic acid myristyl ester,
copolymers of acrylic acid with acrylic acid cetyl ester,
copolymers of acrylic acid with methacrylic acid cetyl ester,
copolymers of acrylic acid with acrylic acid stearyl ester,
copolymers of acrylic acid with methacrylic acid stearyl ester,
copolymers of acrylic acid with acrylic acid eicosyl ester,
copolymers of acrylic acid with methacrylic eicosyl ester
copolymers of methacrylic acid with acrylic acid methyl ester,
copolymers of methacrylic acid with methacrylic acid methyl ester,
copolymers of methacrylic acid with acrylic acid methyl ester,
copolymers of methacrylic acid with methacrylic acid ethyl ester,
copolymers of methacrylic acid with acrylic acid propyl ester,
copolymers of methacrylic acid with methacrylic acid propyl ester,
copolymers of methacrylic acid with acrylic acid isopropyl ester,
copolymers of methacrylic acid with methacrylic acid isopropyl ester,
copolymers of methacrylic acid with acrylic acid octyl ester,
copolymers of methacrylic acid with methacrylic acid octyl ester,
copolymers of methacrylic acid with acrylic acid decyl ester,
copolymers of methacrylic acid with methacrylic acid cc decyl ester,
copolymers of methacrylic acid with acrylic acid lauryl ester,
copolymers of methacrylic acid with methacrylic acid lauryl ester,
copolymers of methacrylic acid with acrylic acid myristyl ester,
copolymers of methacrylic acid with methacrylic acid myristyl ester,
copolymers of methacrylic acid with acrylic acid cetyl ester,
copolymers of methacrylic acid with methacrylic acid cetyl ester,
copolymers of methacrylic acid with acrylic acid stearyl ester,
copolymers of methacrylic acid with methacrylic acid stearyl ester,
copolymers of methacrylic acid with acrylic acid eicosyl ester,
copolymers of methacrylic acid with methacrylic eicosyl ester
copolymers of acrylic acid and methacrylic acid with acrylic acid methyl ester,
copolymers of acrylic acid and methacrylic acid with methacrylic acid methyl ester,
copolymers of acrylic acid and methacrylic acid with acrylic acid ethyl ester,
copolymers of acrylic acid and methacrylic acid with methacrylic acid ethyl ester,
copolymers of acrylic acid and methacrylic acid with acrylic acid propyl ester,
copolymers of acrylic acid and methacrylic acid with methacrylic acid propyl ester,
copolymers of acrylic acid and methacrylic acid with acrylic acid isopropyl ester,
copolymers of acrylic acid and methacrylic acid with methacrylic acid isopropyl ester,
copolymers of acrylic acid and methacrylic acid with acrylic acid octyl ester,
copolymers of acrylic acid and methacrylic acid with methacrylic acid octyl ester,
copolymers of acrylic acid and methacrylic acid with acrylic acid decyl ester,
copolymers of acrylic acid and methacrylic acid with methacrylic acid cc decyl ester,
copolymers of acrylic acid and methacrylic acid with acrylic acid lauryl ester,
copolymers of acrylic acid and methacrylic acid with methacrylic acid lauryl ester,
copolymers of acrylic acid and methacrylic acid with acrylic acid myristyl ester,
copolymers of acrylic acid and methacrylic acid with methacrylic acid myristyl ester,
copolymers of acrylic acid and methacrylic acid with acrylic acid cetyl ester,
copolymers of acrylic acid and methacrylic acid with methacrylic acid cetyl ester,
copolymers of acrylic acid and methacrylic acid with acrylic acid stearyl ester,
copolymers of acrylic acid and methacrylic acid with methacrylic acid stearyl ester,
copolymers of acrylic acid and methacrylic acid with acrylic acid eicosyl ester and
copolymers of acrylic acid and methacrylic acid with methacrylic acid eicosyl ester.

Particularly preferred agents contain a copolymer of methacrylic acid (MAA) and ethyl acrylate (EA) as copolymer A.

It is preferred for the total amount of copolymers A, based on the weight of the ready-to-use agent, to be from about 0.05 to about 5% by weight, preferably from about 0.1 to about 2% by weight and in particular from about 0.25 to about 1.5% by weight.

A second essential ingredient of the agent for temporary deformation of keratinic fiber is at least one further polymer B from the group containing cationic polymers, that is, the polymers containing the at least one monomer unit having a positively charged group. This cationic polymer is selected from cationic guar derivatives.

Here preferred agents are those which contain, as a cationic polymer B, at least one guar 2-hydroxy-3-trimethylammoniopropylether (INCI name: GUAR HYDROXYPROPYLTRIMONIUM CHLORIDE).

Other quaternized guar derivatives can also be used with preference. A further preferred embodiment of the present disclosure are agents which contain, as a cationic polymer, at least one hydroxypropyl guar 2-hydroxy-3-trimethylammoniopropyl ether (INCI name: HYDROXYPROPYL GUAR HYDROXYPROPYLTRIMONIUM CHLORIDE).

Preferably, the cationic guar derivatives are used within certain amount ranges. Here, preference is given to agents which, based on the weight of the ready-to-use agent, contain from about 0.15 to about 15% by weight, preferably from about 0.3 to about 6% by weight and in particular from about 0.75 to about 4.5% by weight of polymer(s) B.

Agents are preferred in which the weight ratio of copolymer(s) A to polymer(s) B is from about 1:1 to about 1:10, more preferably from about 1:1 to about 1:5, and most preferably from about 1:2 to about 1:4.

A third essential ingredient of the agents for temporary deformation of keratinic fiber is at least one polymer C different than copolymer A and polymer B selected from cationic cellulose derivatives.

The cationic cellulose derivatives are preferably quaternized and, for example, commercially available under the names Celquat® and polymer JR®. The compounds Celquat® H 100, Celquat® L 200 and polymer JR® 400 are preferred quaternized cellulose derivatives.

Celquat® H 100 and Celquat® L 200 (AkzoNobel Surface Chemistry) are referred to as Polyquaternium-4 according to INCI and are preferred cationic cellulose derivatives in the context of the present disclosure. Polyquaternium-4 is a copolymer of hydroxyethylcellulose and diallyldimethylammonium chloride.

A further preferred cationic cellulose derivative is available under the INCI name Polyquaternium-10. It is, for example, available as Celquat® SC-230M or Celquat® SC-240C (AkzoNobel Functional Chemicals) as a commercial product.

Particularly preferred agents contain, as cationic cellulose derivatives, at least one reaction product of hydroxyethylcellulose with trimethylammonium-substituted epoxides (INCI name: POLYQUATERNIUM-10).

In addition, the cosmetic agents can also contain 6-deoxy-6-ammonium celluloses as cationic cellulose derivatives.

Preferably, the cationic cellulose derivative is used within certain amount ranges. Here, preference is given to agents which, based on the weight of the ready-to-use agent, contain from about 0.05 to about 1.5% by weight, preferably from about 0.5 to about 1% by weight and in particular from about 0.3 to about 0.8% by weight of polymer(s) C.

Particularly preferred agents contain, as copolymer A, a copolymer of methacrylic acid (MAA) and ethyl acrylate (EA), as polymer B, Guar Hydroxypropyltrimonium Chloride (INCI) and as polymer C, Polyquaternium-4 (INCI).

Particularly preferred agents contain, as copolymer A, a copolymer of methacrylic acid (MAA) and ethyl acrylate (EA), as polymer B, Guar Hydroxypropyltrimonium Chloride and as polymer C, Polyquaternium-10 (INCI).

The present disclosure is not subject to limitations with regard to the selection of (co)polymers A to C. Both respectively only one polymer and respectively a plurality of polymers from the individual classes described can be used.

Regardless of the type and weight ratio of the polymers to each other, in addition, agents are preferred in which the total polymer content of (co)polymers A to C of the agent is from about 0.6 to about 21.5% by weight, preferably from about 1 to about 15% by weight and in particular from about 2 to about 8% by weight.

The preparation/application of the cosmetic agent takes place in the form of a mousse, a foam or a spray using a propellant (for example, aerosol spray).

Accordingly, a fourth essential ingredient of the agent for temporary deformation of keratinic fibers is at least one propellant.

Suitable propellants (propellant gases) are propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, both individually and in combination. Hydrophilic propellant gases, such as carbon dioxide, can also be used advantageously in the context of the present disclosure, when the proportion of hydrophilic gases is selected low and lipophilic propellant gas (for example, propane/butane) is present in excess. Particularly preferred are propane, n-butane, isobutane and mixtures of these propellant gases. Preferred cosmetic agents are exemplified in that the agent furthermore comprises at least one propellant b) from the group propane, mixture of propane and butane, dimethyl ether and 1,1-difluoroethane (INCI: Hydrofluorocarbon 152a). Preference is given to using a mixture of propane and butane as a propellant.

The amount of propellant is preferably from about 2 to about 12% by weight and more preferably from about 4 to about 8% by weight, each based on the total cosmetic agent.

The cosmetic agent can preferably be constituent of a cosmetic product which further comprises a dispensing device.

Vessels made of metal (aluminum, tinplate, tin), protected or non-splintering plastic or glass, which is coated with plastic on the outside, are considered pressurized gas containers for aerosol applications; pressure and fracture resistance, corrosion resistance, easy ability to fill and aesthetic aspects, handiness, ability to be pressurized etc. play a role in their selection. Special interior protective lacquers ensure corrosion resistance to the cosmetic agent.

If the cosmetic products are to be sprayed on the hair, these agents are advantageously added to a dispensing device having a spray valve. The resulting cosmetic products accordingly comprise a cosmetic agent and a dispensing device having a spray valve.

The agents contain the polymers and the propellant in a cosmetically acceptable carrier.

Preferred cosmetically acceptable carriers are aqueous, alcoholic or aqueous-alcoholic media having preferably at least about 10% by weight of water, based on the total agent. It is possible in particular to include the lower alcohols having 1 to 4 carbon atoms usually used for cosmetic purposes, such as, for example, ethanol and isopropanol, as alcohols.

As additional co-solvents, organic solvents or a mixture of solvents having a boiling point below about 400° C. can be present in an amount of from about 0.1 to about 15% by weight, preferably from about 1 to about 10% by weight, based on the total agent. Particularly suitable as additional co-solvents are unbranched or branched hydrocarbons such as pentane, hexane, isopentane and cyclic hydrocarbons such as cyclopentane and cyclohexane. Furthermore, particularly preferred water-soluble solvents are glycerol, ethylene glycol, butylene glycol, sorbitol and 1,2-propanediol in an amount of up to about 30% by weight based on the total agent.

The agents preferably have a pH value of from about 2 to about 11. Particularly preferred is the pH range between about 2 and about 8. In the context of this document, the pH values refer to the pH at about 25° C., unless stated otherwise.

Further constituents of the agent for temporary deformation of keratinic fibers are described in the following, which can be included in the agents in addition to the above-described mandatory ingredients.

It can be preferred that the agent for temporarily deforming keratinic fibers further comprises chitosan.

Chitosans are biopolymers and are counted among the group of hydrocolloids. Chemically considered, these are partially deacetylated chitins of different molecular weight. One starts from chitin, preferably the shell remnants of crustaceans, which are available as cheap raw materials in large quantities, for the production of chitosans. The chitin in this case is usually first deproteinized by the addition of bases, demineralized by the addition of mineral acids and finally deacetylated by the addition of strong bases, wherein the molecular weights can be distributed over a broad spectrum. Preferably used are those types having an average molecular weight of from about 800,000 to about 1,200,000 daltons, a Brookfield viscosity (1% weight in glycolic acid) below about 5000 mPas, a degree of deacetylation in the range of from about 80 to about 88%, and having an ash content of less than about 0.3% by weight.

It is also possible to use cationically derivatized chitosans (such as quaternization products) or alkoxylated chitosans. Accordingly, the term "chitosan" includes chitosan or its derivatives.

Suitable chitosans, for example, are freely commercially available under the trade names Hydagen® CMF (about 1% by weight of active substance in aqueous solution with about 0.4% by weight of glycolic acid, molecular weight from about 500,000 to about 5,000,000 g/mol; Cognis), Hydamer® HCMF (Chitosan (about 80% deacetylated), molecular weight from about 50,000 to about 1,000,000 g/mol, Chitinor, formerly Cognis), Kytamer® PC (about 80% by weight of active substance of chitosan pyrolidon-carboxylat (INCI name: Chitosan PCA), Amerchol), Chitolam® NB/101 and Chitosan 90/100/A1® (chitosan (about 90% deacetylated); BioLog Heppe).

The chitosan is present in preferred agents, based on their total weight, in a total amount of from about 0.01 to about 1.5% by weight, preferably from about 0.1 to about 1% by weight. Particularly preferred is the use of non-derivatized chitosan.

Particularly preferred agents contain, as copolymer A, a copolymer of methacrylic acid (MAA) and ethyl acrylate (EA), as polymer B, Guar Hydroxypropyltrimonium Chloride (INCI), as polymer C, Polyquaternium-4 (INCI) and chitosan, preferably non-derivatized chitosan.

It can be preferred that the agent for temporarily deforming keratinic fibers further comprises care substances for keratinic fiber, in particular human hair, and/or human skin, in particular scalp. These can in particular comprise D-panthenol, L-arginine, Dimethicone (INCI), Amodimethicone (INCI), vitamins, vitamin derivatives, protein hydrolyzate, collagen hydrolyzate and/or nicotinic acid amide.

As mentioned at the outset, the cosmetic agents described above are distinguished by particular hair cosmetic properties, in particular advantageous properties in temporary hair deformation. A third subject of the present application is therefore the use of an agent or product as contemplated herein for temporary deformation of keratinic fibers, in particular human hair.

A fourth subject of the present application is a method for temporary deformation of keratinic fibers, in particular human hair, in which the keratinic fibers are acted upon by a cosmetic agent as contemplated herein and temporarily fixed in their shape.

With regard to further preferred embodiments of the use and the method, what has been said about the cosmetic agents applies mutatis mutandis.

EMBODIMENTS

Unless otherwise stated, the following amount specifications are in percent by weight of active substance.

Products

The styling agent E1 as contemplated herein and the styling agent V1 not as contemplated herein were prepared according to Table 1 below. The name of the ingredients was partly based on their INCI.

TABLE 1a

Composition styling agent

| Raw materials | E1 | V1 |
| --- | --- | --- |
| MAA/EA | 1 | — |
| Guar Hydroxypropyltrimonium Chloride | 3 | — |
| Chitosan | 0.3 | 0.3 |
| Polyacrylamidopropyltrimonium Chloride | 0.2 | 0.2 |
| Polyquaternium-4 | 0.45 | 1.35 |
| PVP (K-90) | — | 1 |
| Cetrimonium Chloride | 0.25 | 0.25 |
| Castor Oil hydrog. 40 EO | 0.2 | 0.2 |
| D-Panthenol | 0.1 | 0.1 |
| Lactic acid | 0.22 | 0.22 |
| Perfume | 0.2 | 0.2 |
| Preservative | 0.5 | 0.3 |
| Propane/butane | 6 | 6 |
| Water, demineralized | ad 100 | ad 100 |

The cosmetic products prepared were tested for their moisture resistance by employing the HHCR test (high humidity curl retention tests).

For this purpose, 10 hair strands (European natural, type 827560, tied on one side, not glued, color 6/0, length 240 mm, weight~0.6 g, $L_{max}$=220 mm, Kerling Internationale Haarfarbrik GmbH) per cosmetic V1 and E1 were prepared by applying 180 mg of the respective cosmetic product to the hair strands and massaged in by hand. The hair strands were then wound on winders (length 160 mm, diameter 10 mm) and dried overnight at 298 K and 50% relative humidity. The hair strands were fastened to a metal frame after being unwound, placed in a climatic chamber at 298 K and 85% relative humidity and their length determined directly afterwards by employing a laser (corresponds to the value $L_0$). After a further 6 h, the length of the hair strands was determined again (corresponds to value $L_t$).

The moisture resistance, that is, the HHCR value, is calculated on the basis of the values determined according to the following equation:

$$HHCR = \frac{L_{max} - L_t}{L_{max} - L_0} * 100$$

The following table shows the HHCR values for the cosmetic products V1 and E1.

|  | V1 | E1 |
|---|---|---|
| HHCR [%] | 39 | 52 |

The HHCR value determined for the cosmetic product E1 is significantly higher than the HHCR value determined for the cosmetic product V1. By using the combination of an anionic copolymer A based on selected acrylate monomers (here: MAA and EA) with a cationically modified guar derivative B instead of polyvinylpyrrolidone, an increase in the moisture resistance of cosmetic agents for temporary deformation of keratinic fibers, in particular human hair, is achieved.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for temporary deformation of human hair, consisting of in a cosmetically acceptable carrier:
  a) a copolymer of methacrylic acid and ethyl acrylate in an amount, based on the weight of the agent, of from about 0.05 to about 5% by weight,
  b) guar hydroxypropyltrimonium chloride in an amount, based on the weight of the agent, of from about 0.15 to about 15% by weight;
  c) Polyquaternium-4 in an amount, based on the weight of the agent, of from about 0.05 to about 1.5%;
  d) at least one propellant in an amount, based on the weight of the agent, of from about 2 to about 12% by weight;
  e) chitosan in an amount, based on the weight of the agent, of from about 0.01 to about 1.5% by weight; and
  optionally,
    polyacrylamidopropyltrimonium chloride;
    cetrimonium chloride;
    castor oil hydrogenated with 40 ethylene oxide;
    d-panthenol;
    lactic acid;
    perfume; and
    preservative.

2. A cosmetic product comprising:
  i. an agent for temporary deformation of hair according to claim 1, and
  ii. a dispensing device.

3. The cosmetic agent for temporary deformation of hair according to claim 2, wherein the dispensing device is a spray valve.

4. A method for temporary deformation of hair, comprising:
  exposing the hair to a cosmetic agent according to claim 1; and
  temporarily fixing the hair in shape.

* * * * *